(12) United States Patent
Amir et al.

(10) Patent No.: US 10,835,666 B2
(45) Date of Patent: Nov. 17, 2020

(54) CLIP-HOLDER FOR INTRAVENOUS ADMINISTRATION SET

(71) Applicant: AQA Innovations, LLC, Plantation, FL (US)

(72) Inventors: Murtaza Amir, Cumberland, MD (US); Adnan Qayyum, Bethlehem, PA (US); Max Arocha, Plantation, FL (US)

(73) Assignee: AQA Innovations, LLC, Plantation, FL (US)

( * ) Notice: Subject to any disclaimer, the term of this patent is extended or adjusted under 35 U.S.C. 154(b) by 0 days.

(21) Appl. No.: 16/021,676

(22) Filed: Jun. 28, 2018

(65) Prior Publication Data
US 2020/0001003 A1 Jan. 2, 2020

(51) Int. Cl.
| | | |
|---|---|---|
| *F16L 3/13* | (2006.01) | |
| *F16L 3/12* | (2006.01) | |
| *A61M 5/14* | (2006.01) | |
| *C09J 7/30* | (2018.01) | |
| *C09J 7/40* | (2018.01) | |
| *C09J 5/00* | (2006.01) | |
| *H02G 3/20* | (2006.01) | |
| *F16L 3/223* | (2006.01) | |
| *F16M 13/02* | (2006.01) | |
| *H02G 3/00* | (2006.01) | |

(52) U.S. Cl.
CPC ........ *A61M 5/1418* (2013.01); *A61M 5/1415* (2013.01); *C09J 5/00* (2013.01); *C09J 7/30* (2018.01); *C09J 7/403* (2018.01); *A61M 2209/06* (2013.01); *F16L 3/13* (2013.01); *F16L 3/2235* (2013.01); *F16M 13/022* (2013.01); *H02G 3/266* (2013.01)

(58) Field of Classification Search
CPC .............. A61M 5/1418; A61M 5/1415; A61M 2209/06; C09J 7/30; C09J 7/403; C09J 5/00; F16M 3/13; F16M 3/2235; F16M 13/022
USPC ......... 248/205.3, 74.2, 74.3, 316.7; 604/174, 604/180; 24/306, 336, 129 R; 128/DIG. 26
See application file for complete search history.

(56) References Cited

U.S. PATENT DOCUMENTS

| | | | | | |
|---|---|---|---|---|---|
| 3,630,195 | A | * | 12/1971 | Santomieri | A61M 25/02 128/DIG. 26 |
| 3,659,319 | A | * | 5/1972 | Erickson | D05B 51/00 24/304 |
| 3,696,920 | A | * | 10/1972 | Lahay | A61B 50/20 128/DIG. 26 |
| 4,025,015 | A | * | 5/1977 | Kolic | F16L 3/08 248/205.3 |
| 4,840,337 | A | * | 6/1989 | Zaugg | B62J 6/02 248/115 |
| 5,323,992 | A | * | 6/1994 | Sifers | A61M 5/1418 24/129 R |
| 5,681,290 | A | * | 10/1997 | Alexander | A61M 25/02 604/174 |
| 5,800,402 | A | * | 9/1998 | Bierman | A61M 25/02 128/DIG. 26 |

* cited by examiner

*Primary Examiner* — Tan Le
(74) *Attorney, Agent, or Firm* — Ted W. Whitlock (57) ABSTRACT

A clip-holder device for retaining and positioning an IV set tubing, and methods for using and kits including the clip-holder device.

15 Claims, 13 Drawing Sheets

CLIP-HOLDER FOR INTRAVENOUS ADMINISTRATION SET

BACKGROUND OF THE INVENTION

The present invention relates to a device for organizing and holding in place, tubing used in connection with an intravenous (IV) administration set, as commonly used in the medical and infusion therapy fields. An IV administration set, also referred to as an IV set, is used by a physician or other medical professional or practitioner (hereinafter, a "user") to deliver to or retrieve from a patient a fluid, such as blood, a medicament, a nutritional supplement, a solution, or the like.

The IV set generally includes a section of intravenous tubing having a first end for communicating with a fluid reservoir, and a second or terminal end adapted for insertion into the patient. For example, the terminal end may include an adaptor for attaching a hypodermic needle. The IV set may further include various components positioned along the section of intravenous tubing, such as components designed to control the flow of or treat the fluid within the IV set during the infusion process. For example, the IV set components may include clamps, filters, chambers, access ports, stopcocks, valves, pumps, monitors, or the like. Additionally, the IV set may include a plurality of intravenous tubing lines.

The tubing, or "lines" used in connection with an IV administration set can range in length, and typically ranges from 24 to 120 inches in length. While in use, such as during administration of a fluid or medicament to a patient, the tubing length allows for movement of the patient relative to the stationary fluid source. Current packaging techniques typically require the user to unroll and untangle the IV set prior to use.

In use, the IV set tubing is typically allowed to hang loosely between the fluid source and the patient to allow for maximum extension and free positioning of the tubing, or the tubing can be placed or looped behind a fixture such as a bed frame or railing to keep it out of the way and prevent the tubing from interfering with access to the patient for performing a procedure on the patient. However, during use, the tubing can become tangled or can be in the way of the user needing to perform a procedure on the patient.

Clips for holding the tubing in place ("clip-holders") can be provided; however, clips that are permanently positioned do not provide the capability to be re-positioned when placement of the tubing needs to be changed. Accordingly, permanently affixed clip-holders can present disadvantages in normal use.

Moreover, clip-holders that are detachably affixed to one surface are not readily moved or re-positioned to another type of surface. For example, a clip-holder detachably affixed to a metal surface may not be easily re-positioned to another type of surface, e.g., a fabric, plastic, wood, or skin surface. Additionally, a clip-holder for affixing to a flat surface cannot be readily affixed to a curved or rounded surface, such as an IV pole, and do not provide good adhesion to such surfaces. Nor can a clip-holder configured for affixing to a rounded or curved surface be readily affixed to a flat surface.

While clip-holders for IV set tubing are available and exist, what is needed is a clip-holder for positioning and retaining IV set tubing, wherein the clip-holder can be readily and detachably affixed to either a flat or a rounded or curved surface, as needed, regardless of the material forming the surface, to position the IV set tubing in any convenient and desired location so the tubing is out of the way of the user so and a procedure can be performed on a patient without interference or encumbrance by the tubing.

BRIEF SUMMARY OF THE INVENTION

The present invention relates to a device and system and method for organizing tubing for an intravenous (IV) administration set, as commonly used in the medical and infusion therapy fields. An IV administration set is used to deliver to or retrieve from a patient a fluid, such as blood, a medicament, a nutritional supplement, or a solution.

More specifically, the present invention relates to a device for retaining and positioning an IV set tubing in a location remote from a medical procedure area. A device of the invention comprises a substrate layer having a front and back face, and a substantially stationary retaining clip portion disposed on or formed integrally with, and jutting away from, the surface of the front face of the substrate layer. The retaining clip portion is configured for receiving and retaining an intravenous tubing without substantially impeding flow of fluid through said tubing. The substrate layer can be rigid or pliable, and the retaining clip portion is preferably rigid, meaning that it generally retains its position and configuration and shape to hold an IV tubing in place during use.

It would be understood that a rigid substrate layer or retaining clip portion can have some flexibility to provide for slight movement of the component by hand wherein, for example, the clip-holder can be briefly and slightly moved for allowing placement of the IV tubing within its hold, and wherein the rigidity of the component causes the component to return to its original shape and configuration. On the other hand, a pliable substrate layer is less rigid, and allows for the component to be bent by hand into a form or shape which is generally retained upon release of pressure causing the bend.

The device comprises backing layer integral with the back face of the substrate layer. The backing layer can comprise an outer adhesive surface for detachably engaging a support structure. Together, the substrate layer and backing layer form a base of the clip-holder. The backing layer preferably can be bonded, and more preferably permanently bonded, to the substrate layer.

Being bonded onto the substrate layer, the backing layer has an outer surface comprising an adhesive for adhering to a support structure. Preferably, the adhesive surface is comprised of an adhesive material that can adhere to a surface of varying materials, including ceramic, metal, plastic, wood, fabric, such as clothing of a patient, or to a patient's skin, and has adhesive strength sufficient to remain in place until removed by the user. The adhesive material is also preferably a detachable or removable adhesive that allows the adhesive surface to be detached or removed from the support surface easily and without marring, marking, or permanent damage to, the support surface upon its removal.

The adhesive surface of the backing layer can be covered by a layer or sheet of material having a non-adhesive outer surface and an inner surface which can be easily removed from the adhesive surface, thereby providing a protective layer over the adhesive layer when not in use. The protective layer is preferably a peel-off layer which can be easily and readily removed prior to use of the clip-holder.

The retaining clip portion juts outwardly from the front face of the substrate layer and is configured, for example, as a hook or prong, which is configured to provide a holding area for receiving and retaining an intravenous tubing without substantially impeding flow of fluid through said tubing.

In certain embodiments, the base can include a plurality of retaining clip portions, and in various configurations for holding several IV administration tubing in place using a single clip-holder device.

Advantageously, substrate layer and backing layer form a base which conforms, as desired, to a flat surface or can be manipulated to conform to a rounded or curved surface of a support structure. Thus, the base can be pliable to conform to the shape of the support structure, or the substrate layer or backing layer, or both, can be formed of a substantially rigid material. Preferably, the backing layer is formed from a pliable material and the substrate layer is formed of a rigid material, such as a hard plastic. The substrate layer can include one or more relief cuts allowing the base to conform to a rounded or curved surface of a support structure, such as an IV pole or IV stand.

In one preferred embodiment, the substrate layer of the base comprises a substantially rigid material, having one or more relief cuts to allow it to conform to a rounded or curved surface of a support structure, and comprises a backing layer that is pliable, and can be bent with or without requiring a relief cut, wherein the substrate layer and backing layer together form a base which can function to conform to a rounded or curved surface for adhering the device to the rounded or curved surface. By bending of the base, the adhesive surface can contact a greater surface area on a rounded or curved support structure than if the base is not bent to shape, and thereby improve adhesion to the support structure. Advantageously, this embodiment can be conformed to fit and tightly adhere to a cylindrical support structure, such as an IV pole.

A most preferred embodiment comprises relief cuts which are straight cuts, or can be formed in the substrate layer as a groove, having a cross-sectional V-shape or U-shape. The relief cuts preferably extend completely across the outer face of the substrate layer. The depth of the relief cuts extends from the outer surface of the substrate layer but preferably do not reach completely through the substrate layer. These relief cuts are generally more than 50% through the height or thickness of the substrate layer and are typically about 75% to 99% through the thickness or height of the substrate layer.

In one preferred embodiment, at least two the relief cuts are formed in the substrate layer and positioned to provide a plurality of sections of the substrate layer, preferably three sections which form a central section, and right and left sections. The width of each of these sections can be equal in size or can be unequal in size, as desired. In one embodiment, each of the right and left sections are equal in size and the central section is narrower in size than the right and left sections.

Preferably, the retaining clip portion or portions are affixed or formed integrally with the substrate layer. More preferably, in an embodiment comprising relief cuts in the substrate layer, the retaining clip portion is affixed to or integrally formed with the right or left sections of the substrate layer. When the device comprises more than one retaining clip portion and two relief cuts to form right, left and central sections of the substrate layer, the retaining clip portion is affixed to or integrally formed with the right and left sections of the substrate layer. Other embodiments comprise retaining clip portions affixed to the central section of the substrate layer when relief cuts are present in the substrate layer. Still other embodiments comprise retaining clip portions affixed to each of the central, left and right sections of the substrate layer.

To facilitate removal of the device of the invention from the support structure onto which it has been adhered, the substrate layer can also include one or more tabs which remain unadhered to the support structure, and which provide leverage for removing the adhered device from the support structure. The one or more tabs are generally formed contiguous with the substrate layer and extend beyond an edge of the backing layer. These one or more tabs can be substantially flat or slightly curved or angled upwardly, in the direction of the outer face of the substrate layer, to allow a user to reach under the tab and remove the device from the support structure by hand, e.g., using a fingertip or prying instrument. Advantageously, a tab configured in an upwardly curved shape can facilitate positioning of the tubing within the retaining clip portion, serving as a guide for placement of the tubing within the hold area formed by the retaining clip portion.

In one embodiment of the invention, a system is provided wherein the clip-holder can be packaged together with a standard IV administration set, as a kit. The system or kit can further comprise written instructions for using the device in conjunction with the IV administration set. The written instructions may be information to access electronically stored instructions. In another embodiment of the invention, a plurality of clip-holders can be packaged together, or provided in bulk, with or without an IV administration set, so that a user can carry and readily access one or a few clip-holders of the invention from a plurality of clip-holders as desired for use. In a preferred embodiment, a device of the invention comprises sterilizable material and the device can be individually packaged to retain its sterility until use. Another preferred embodiment of a device of the invention is made to be disposable so that contamination is minimized by the single-use only of the device, compared to contamination that can occur by using the clip-holder multiple times.

Having a readily available package of a plurality of disposable clip-holders can be advantageous for a single use of the device, which can then be disposed of or thrown away when a procedure is completed, and the clip-holder device is no longer needed. Alternatively, a clip-holder device of the invention can be individually packaged and accessed as needed.

In a method of use, a device of the invention can be provided, the adhesive backing exposed and positioned at any convenient site on a support surface, whether that support surface is flat, rounded or curved. When a procedure requires a re-positioning of the clip-holder, the user can remove or detach the clip-holder from that support surface and move the clip-holder to a support surface which is the same (being the same material and configuration, such as flat, rounded, or curved), or different (being a different surface material or a different configuration, such as moving from a flat surface to a rounded, or curved surface, or vice versa). The subject clip-holder advantageously adheres well to the support surface it is re-positioned to, and preferably can be readily removed from the support surface without marring, marking, or damaging the support surface from which it was re-positioned.

Thus, the subject invention provides an advantageous and inexpensive device for organizing IV administration tubing to reduce tangling of or interference by the tubing during medical procedures, and wherein the device can be easily disposed onto and re-positioned onto virtually any support surface without harm to the support surface. Other advantages and applications of a device or system of the invention will be recognized and understood by persons of ordinary skill in the art in view of the detailed description and drawings provided herewith.

BRIEF DESCRIPTION OF THE SEVERAL VIEWS OF THE DRAWINGS

The features and advantages of the invention will be readily understood by reference to specific embodiments which are illustrated in the appended drawings. These drawings depict only typical embodiments of the invention and are not to be considered as limiting the scope of the invention.

DETAILED DESCRIPTION OF THE INVENTION

The preferred embodiments of the present invention may be understood by the description provided herein, along with reference to the drawings. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed but is merely representative of presently preferred embodiments of the invention.

Figure 1:
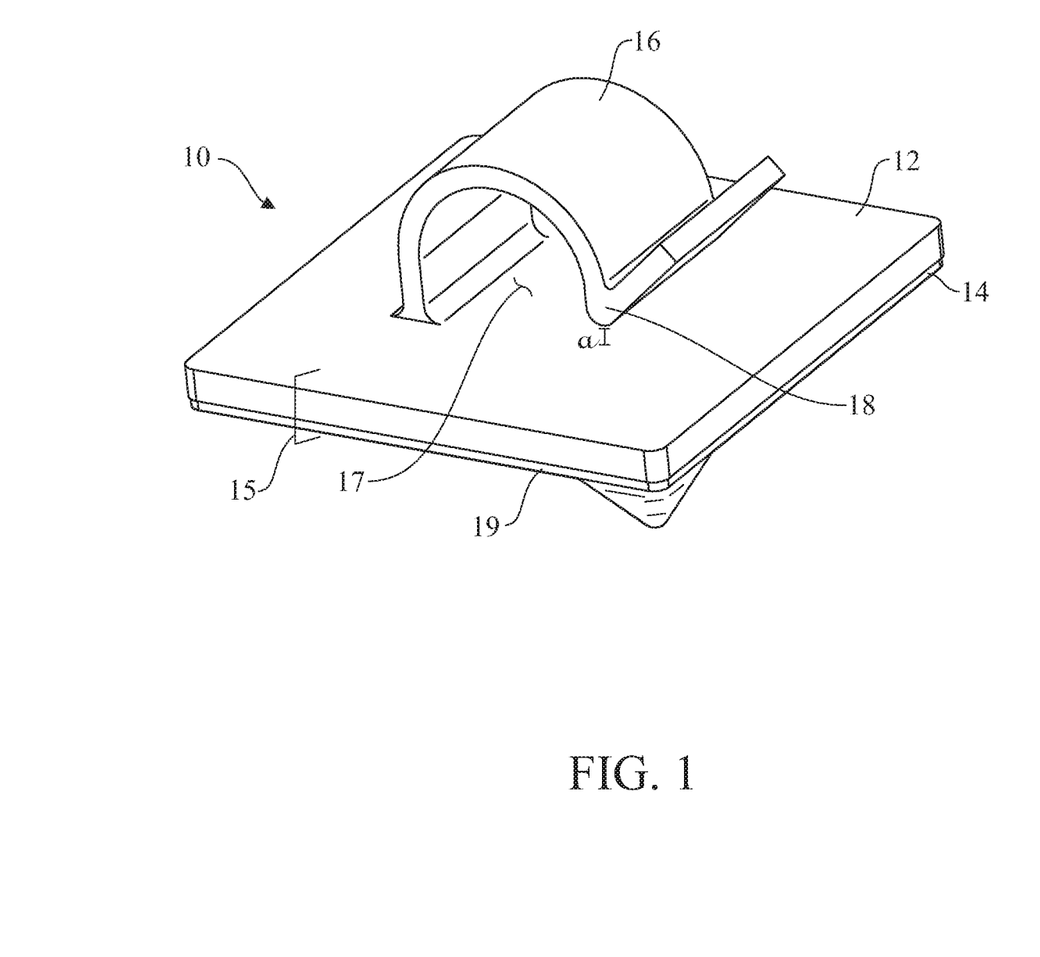
FIG. 1 is a perspective view of an embodiment of a clip-holder device according to the subject invention, illustrating the substrate layer and backing layer forming the substantially flat base, and a single retaining clip portion integral with the substrate layer.

Referring to FIG. 1, an embodiment of a clip-holder device 10 of the invention is shown in perspective view to illustrate the basic elements of the invention, namely the substrate layer 12 and backing layer 14 forming the substantially flat base 15 and a single retaining clip portion 16. As shown, the base is substantially rectangular or square; however, it would be understood in the art that other shapes of the base can be formed without detracting from the function and utility of the invention.

Backing layer 14 is preferably bonded to the substrate layer on its inner face, which contact the substrate layer, and comprises an adhesive surface on its opposing, outer face. Adhesive material for use in conjunction with a clip-holder of the subject invention are well-recognized and readily known in the art. Such adhesive materials are commercially available and include glue, epoxy, polymeric adhesives, and the like. Preferably, an adhesive used in connection with the subject invention is a non-permanent or removable adhesive which can be removed without marring or damaging the support surface onto which it is adhered. For example, stretch release adhesive or COMMAND® Adhesive, available from 3M Company (St. Paul, Minn., USA) can be applicable as a removable adhesive used for the subject clip-holder.

In addition, one preferred embodiment comprises a cover material or sheet 19 that can be disposed over the adhesive surface of the backing layer for protecting the adhesive surface and preventing its inadvertent adhesion prior to use.

Retaining clip portion 16 is configured in a shape so that it forms a holding area 17 which is large enough to receive and retain at least one standard IV tubing without crimping or closing of the inner opening of the tubing. The retaining clip portion preferably is shaped as a hook wherein the holding area is not a completely closed loop, having an opening for inserting an IV tubing therethrough. As shown, the retaining clip portion can be formed having a curved shape, wherein a first end of the retaining clip connecting to the substrate layer curves upwardly and away from, then back toward, the substrate layer to which the retaining clip portion is connected, and at a second or terminal end is angled or curved in an opposite direction, forming a retaining lip 18 which provides an opening as gap a between the retaining lip and the outer surface of the substrate layer. By forming gap a having a distance just slightly less than the outer diameter of a standard IV tubing, this feature can help to retain the IV tubing within the holding area of the retaining clip portion.

This embodiment is shown without relief cuts; accordingly, a device which is free of relief cuts and made of substantially rigid material can preferably be adhered to a substantially flat surface. Alternatively, the base comprising a substrate layer and a backing layer can be made from a pliable material so that the base can be bent to conform to a rounded or curved surface, such as an IV pole.

FIGS. 2A-2D show perspective views of alternative embodiments of a clip-holder device according to the subject invention, illustrating the substrate layer and backing layer forming the substantially flat base as in FIG. 1, but comprising two or more retaining clip portions in varying configurations.

Figure 2A:
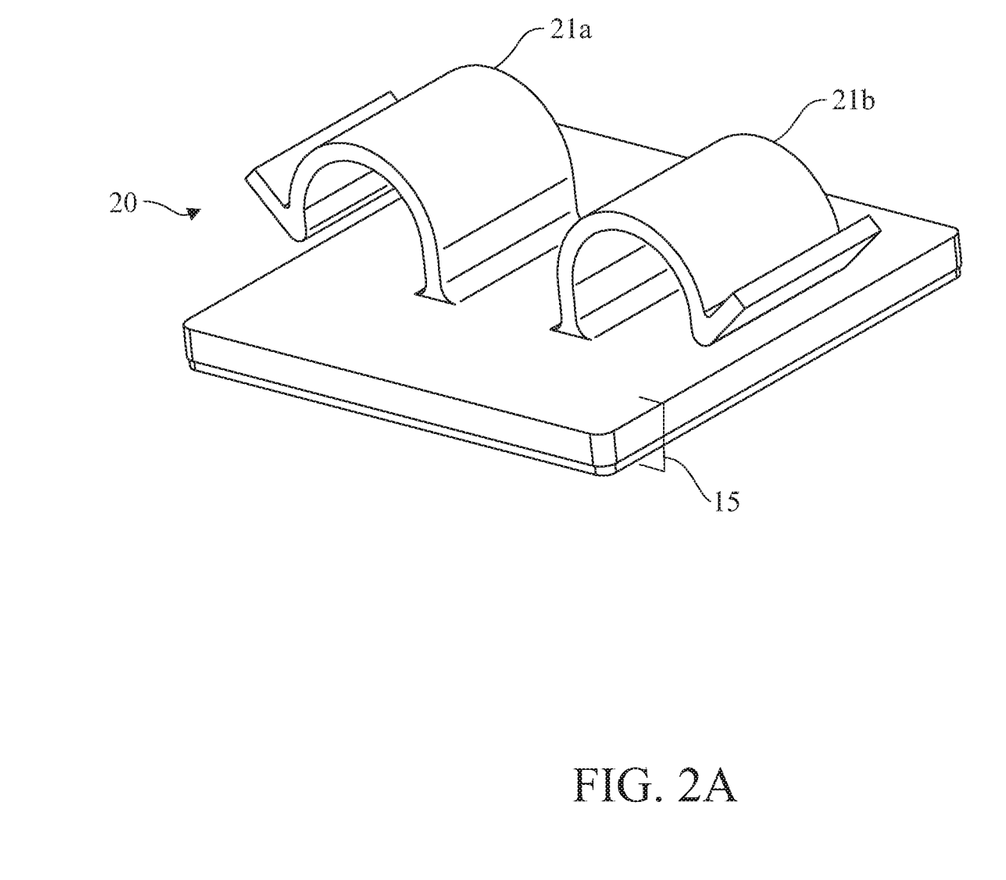
FIG. 2A is a perspective view of an embodiment of a clip-holder device according to the subject invention, illustrating the substrate layer and backing layer forming the substantially flat base, and comprising two retaining clip portions in one configuration.
Figure 2B:
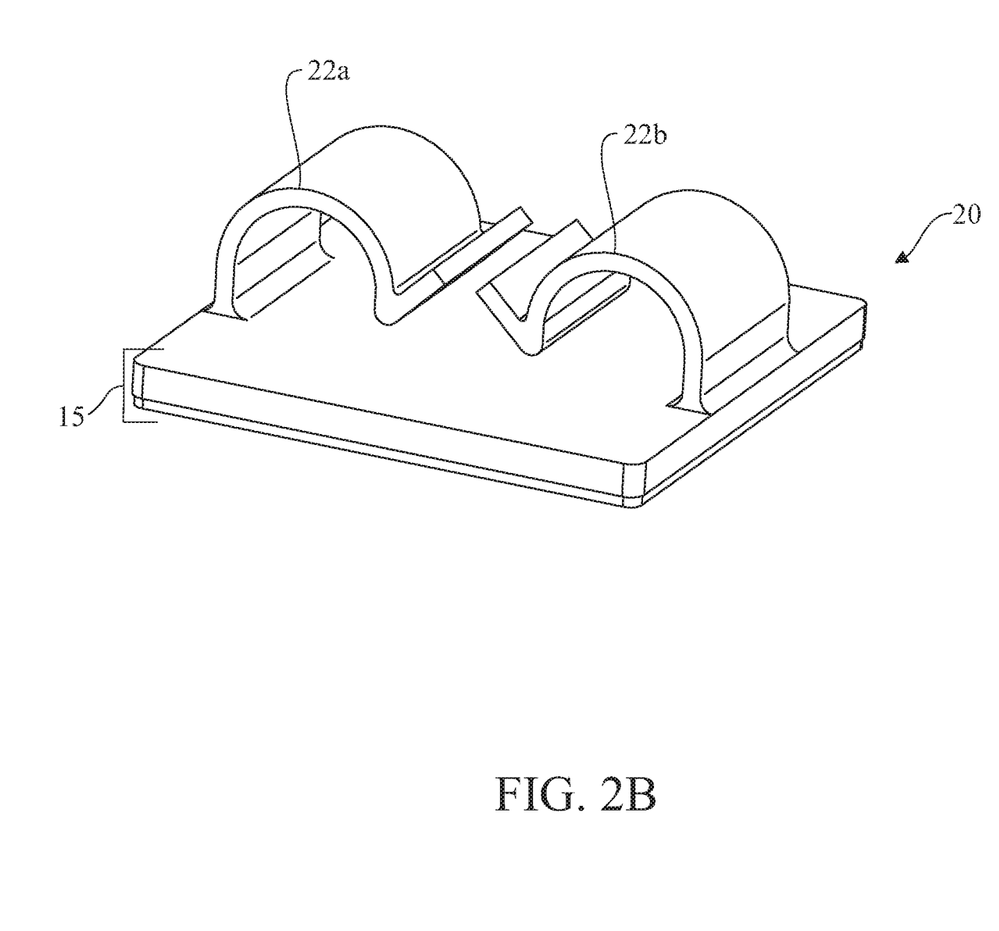
FIG. 2B is a perspective view of an embodiment of a clip-holder device according to the subject invention, illustrating the substrate layer and backing layer forming the substantially flat base, and comprising two retaining clip portions in a configuration different from the configuration shown in FIG. 2A.
Figure 2C:
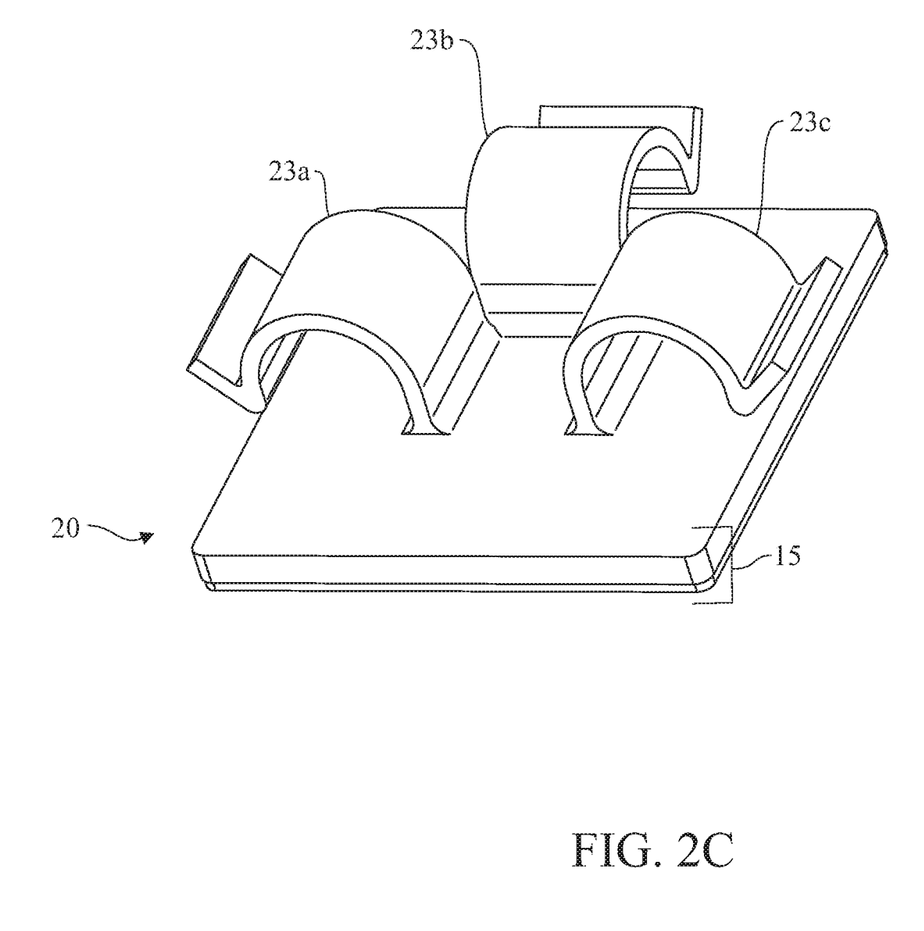
FIG. 2C is a perspective view of an embodiment of a clip-holder device according to the subject invention, illustrating the substrate layer and backing layer forming the substantially flat base, and comprising three retaining clip portions in one configuration.
Figure 2D:
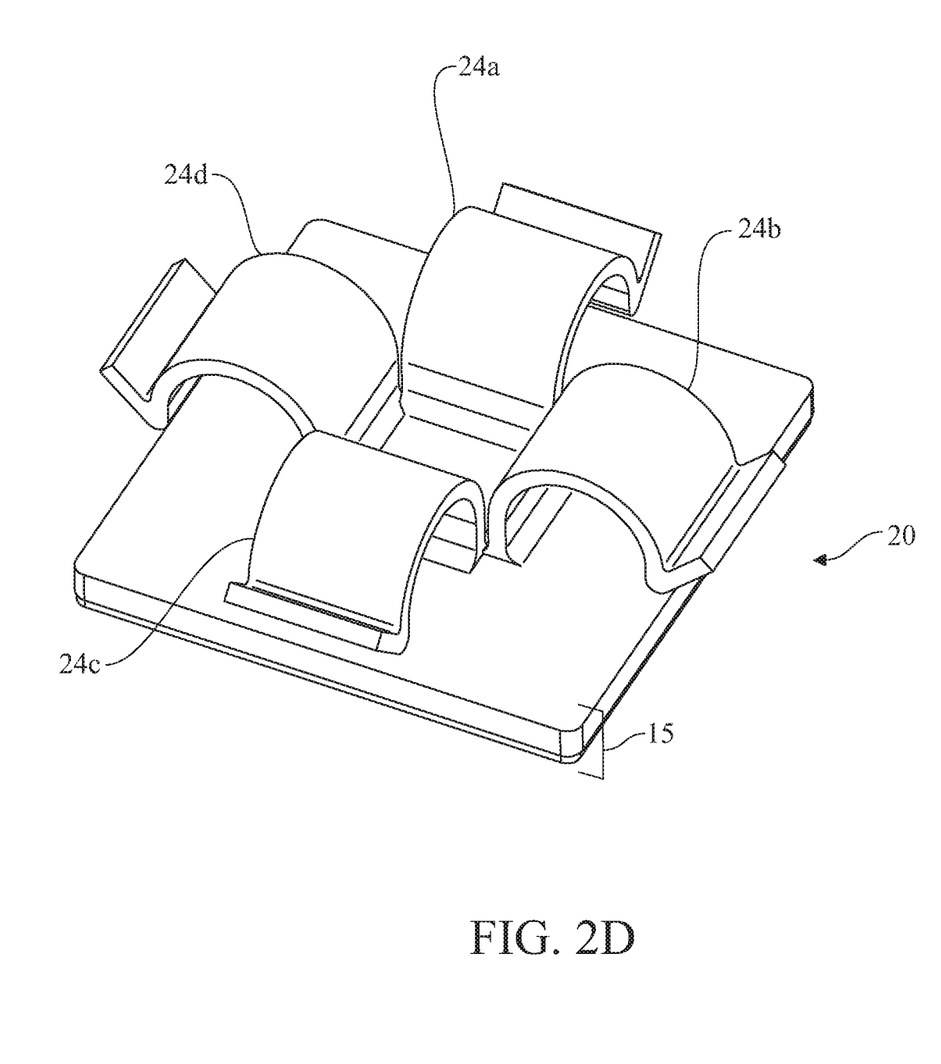
FIG. 2D is a perspective view of an embodiment of a clip-holder device according to the subject invention, illustrating the substrate layer and backing layer forming the substantially flat base, and comprising four retaining clip portions in one configuration.

For example, FIG. 2A shows an embodiment of clip-holder 20 comprising a base 15 and comprising two retaining clip portions 21a and 21b, each retaining clip portion having openings which oppose one another. FIG. 2B shows an embodiment of clip-holder 20 comprising a base 15 and comprising two retaining clip portions 22a and 22b, each retaining clip portion having openings which face one another. FIG. 2C is a perspective view of an embodiment of a clip-holder device 20 according to the subject invention, comprising a base 15 and comprising three retaining clip portions 23a, 23b, and 23c, each retaining clip portion having openings which oppose one another. It would be understood that the three retaining clip portions can be configured to face one another, akin to the configuration illustrated in FIG. 2B. It would also be understood that the three retaining clip portions may also be configured to be evenly spaced apart from one another in a triangular configuration. FIG. 2D is a perspective view of an embodiment of a clip-holder device 20 according to the subject invention, comprising a base 15 and comprising four retaining clip portions 24a, 24b, 24c, and 24d, each retaining clip portion having openings which oppose one another. It would be understood that the four retaining clip portions can be configured to face one another, akin to the configuration illustrated in FIG. 2B. Additional retaining clip portions can be included on a single base, wherein the base is sized to accommodate five or more retaining clip portions, the number of retaining clip portions being limited only by practical considerations and need.

Figure 3:
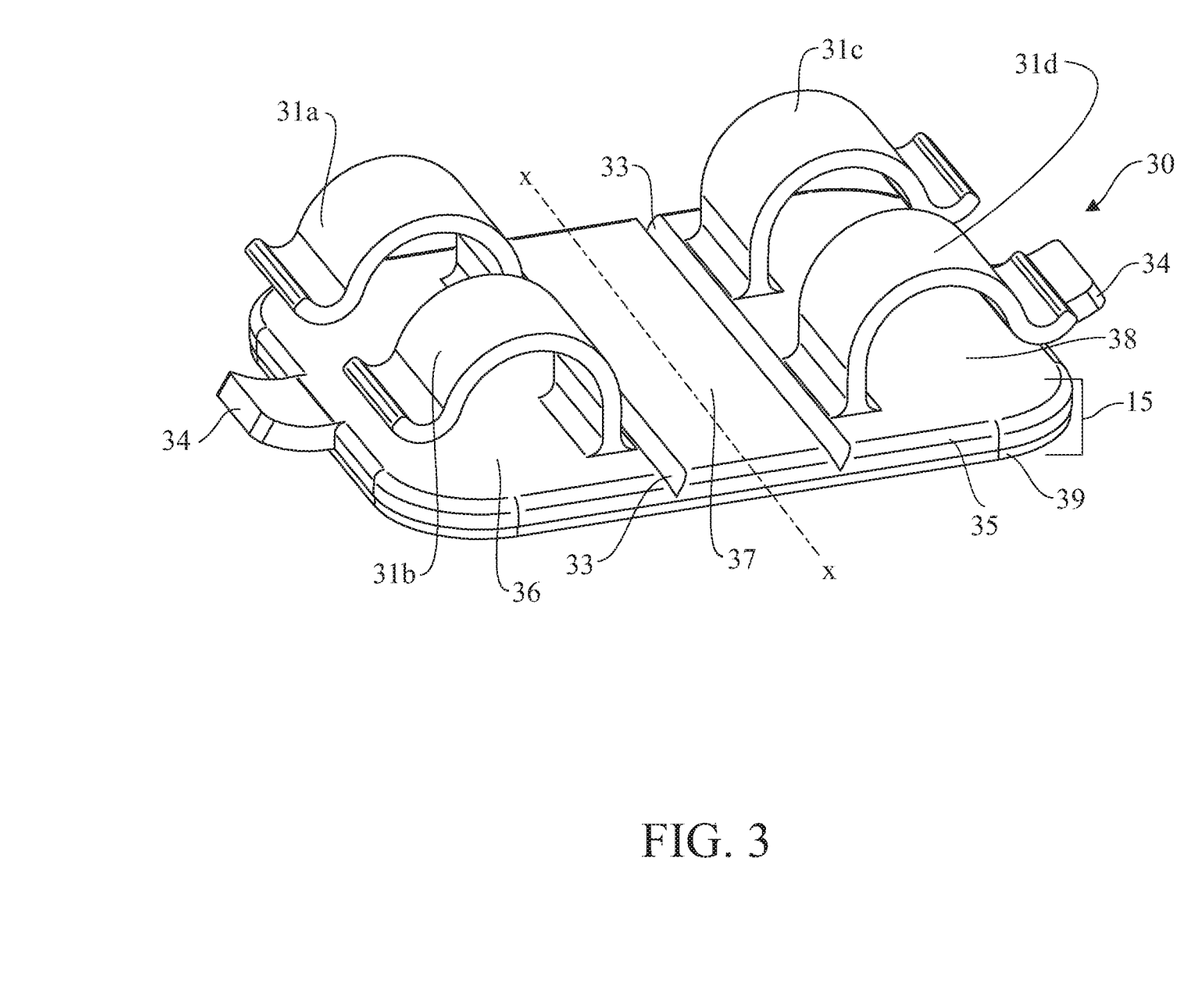
FIG. 3 is a perspective view of an embodiment of a clip-holder device according to the subject invention comprising four retaining clip portions in one configuration, illustrating relief cuts formed in the substrate layer and tabs formed integral with the substrate layer.

FIG. 3 is a perspective view of an embodiment of a clip-holder device 30 according to the subject invention comprising substrate layer 35 and backing layer 39, forming base 15 having four retaining clip portions configured to provide a first pair of retaining clip portions 31a and 31b parallel to one another and having openings opposite from a second pair of parallel retaining clip portions 31c and 31d. FIG. 3 further illustrates an embodiment comprising a relief cut 33 formed in the substrate layer and tab 34 formed integral with the substrate layer of base 15. The embodiment shown in FIG. 3 illustrates two relief cuts 33 formed parallel to one another, providing a sectioned base comprising left section 36, central section 37 and right section 38. This embodiment illustrated in FIG. 3 also shows two tabs 34 at opposing ends of the substrate layer 32, and more specifically, on the outer side edges of right and left sections 36 and 38.

Relief cuts 33 are shown to be configured as V- or U-shaped grooves which extend completely across the dimension of the substrate layer along line x-x. The depth of the groove or grooves forming the one or more relief cuts 33 is substantially through, but is preferably not completely through, the thickness or height of the substrate layer 35. Preferably, the depth of the groove forming the one or more relief cuts is at least 50% through the thickness of the substrate layer, at least 60% through the thickness of the substrate layer, at least 70% through the thickness of the substrate layer, at least 75% through the thickness of the substrate layer, at least 80% through the thickness of the substrate layer, at least 85% through the thickness of the substrate layer, at least 590% through the thickness of the substrate layer, or at least 95% through the thickness of the substrate layer. The depth of the grove forming the one or more relief cuts can be at least 99% through the thickness of the substrate layer or can be 100% through the substrate layer, but not into or not completely through the backing layer.

Further, in the embodiment illustrated in FIG. 3, the retaining clip portions comprise a curved, rather than angled, configuration providing a curved lip portion. This configuration can be advantageous for inserting the tubing into the retaining clip portion hold area.

Figure 4:
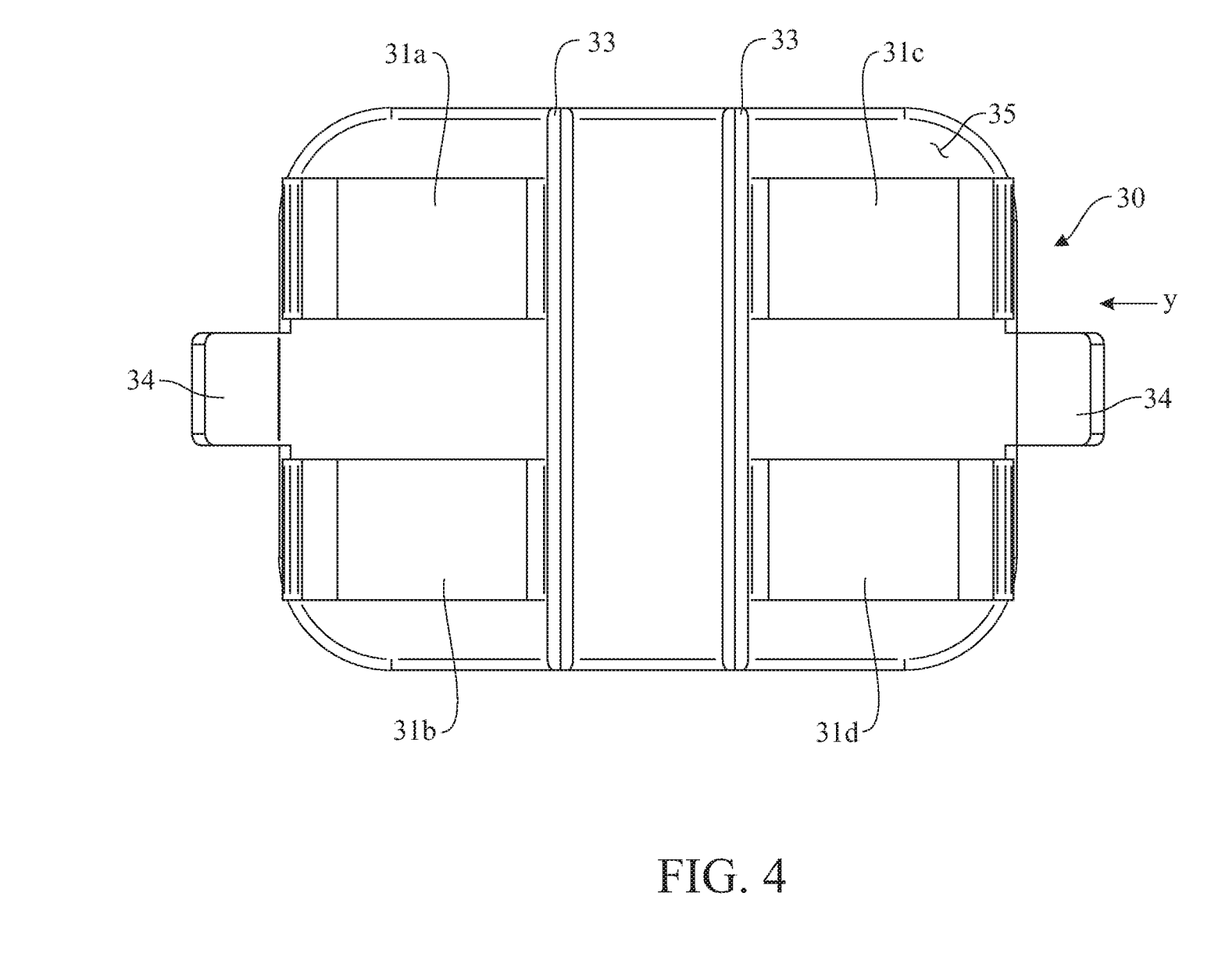
FIG. 4 is a top plan view of the embodiment of a clip-holder device according to the subject invention as shown in FIG. 3.

FIG. 4 is a top plan view of the embodiment of a clip-holder device 30 according to the subject invention as shown in FIG. 3. Illustrated are the top face of the substrate layer 35 having four retaining clip portions 31a, 31b, 31c, and 31d disposed or provided or formed integrally with the substrate layer 35, relief cuts 33 and tabs 34.

Figure 5:
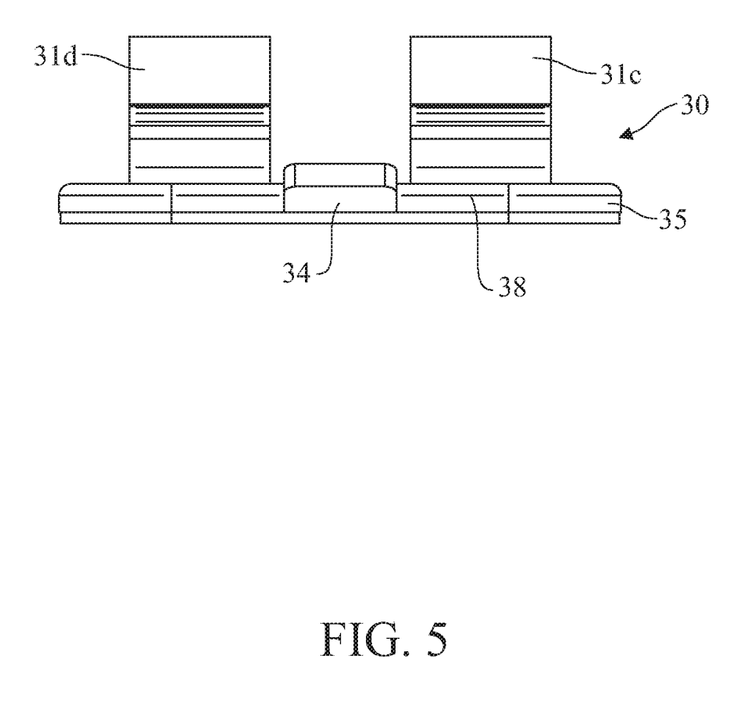
FIG. 5 is a side plan view of the embodiment of a clip-holder device according to the subject invention as shown in FIG. 3, as viewed from the direction along line x-x'.

FIG. 5 is a side plan view of the embodiment of a clip-holder device 30 according to the subject invention as shown and viewed from the direction of arrow y in FIG. 3. of the Illustrated is the right section 38 of substrate layer 35 and showing two retaining clip portions 31c and 31d disposed or provided or formed integrally with an outer surface of substrate layer 35, and tab 34 extending from a side edge of substrate layer. A backing layer is not illustrated in this drawing.

Figure 6:
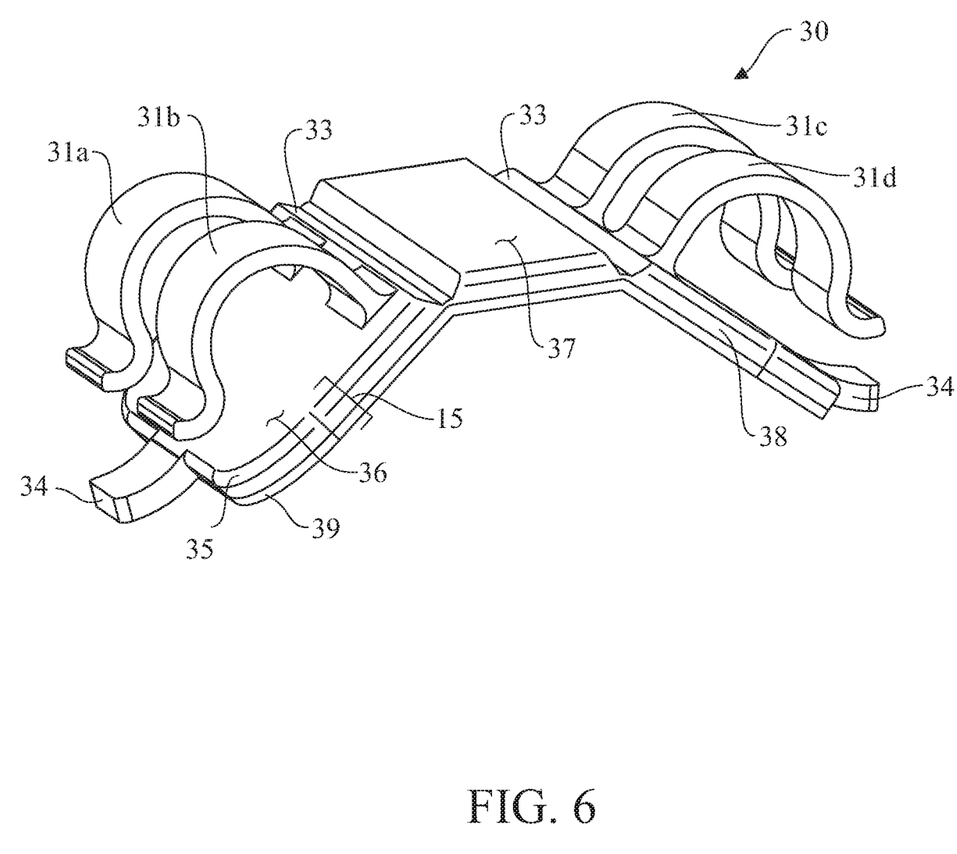
FIG. 6 is a side perspective view of an embodiment of a clip-holder device according to the subject invention, showing a bent configuration which illustrates resulting central, right and left sections of the substrate layer, and four retaining clip portions integral with and affixed to the right and left sections of the substrate layer.

FIG. 6 is a perspective view of an embodiment of a clip-holder device according to the subject invention as illustrated in FIG. 3, showing a bent configuration of the device for advantageously adhering the device to a curved or rounded or cylindrical support surface. The bent configuration shows clip-holder device 30 comprising base 15 formed by substrate layer 35 and backing layer 39, two relief cuts 33 formed parallel to one another, providing a sectioned base comprising left section 36, central section 37 and right section 38, and two tabs 34 at opposing outer side edges of right and left sections 36 and 38.

Figure 7:
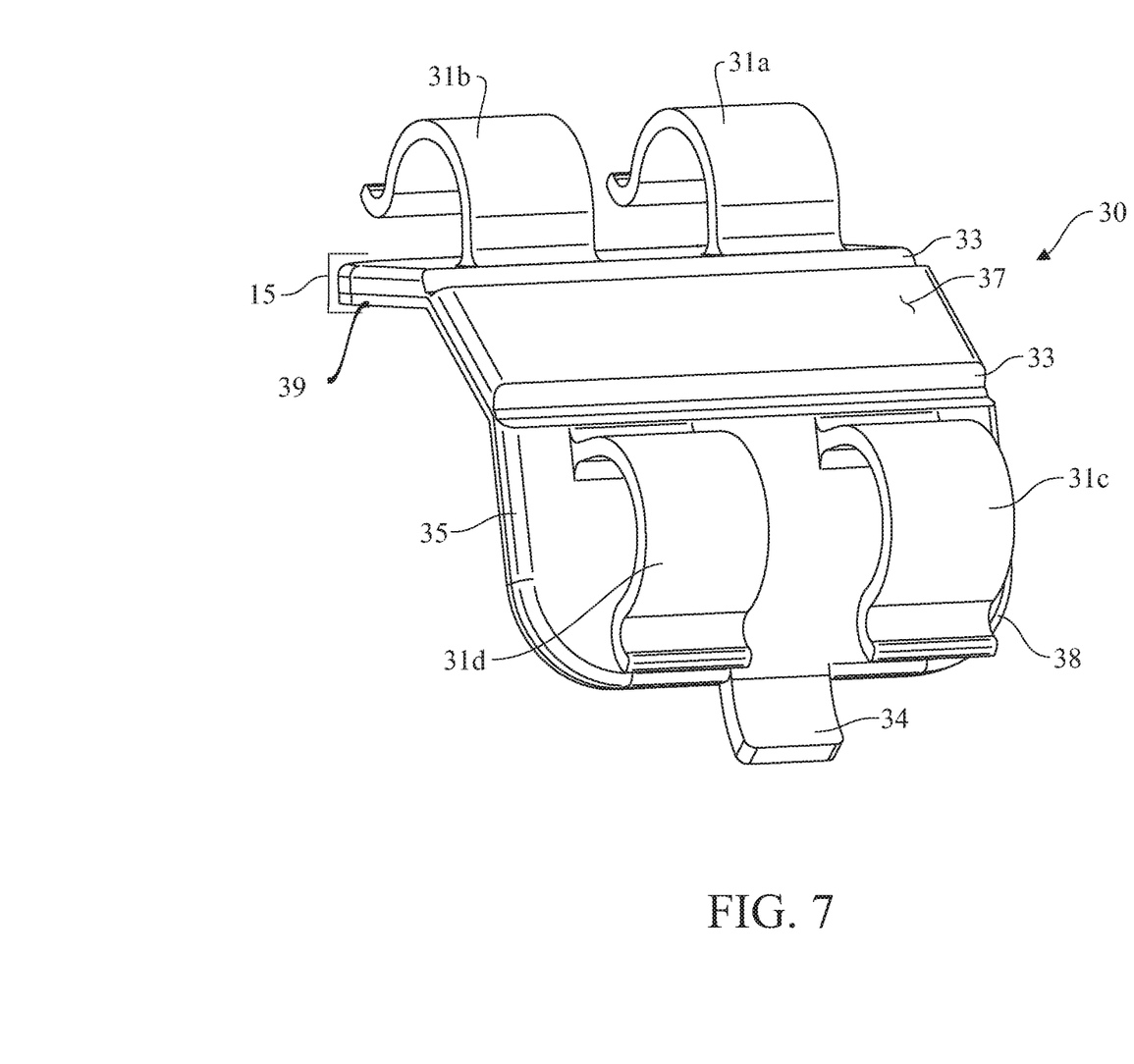
FIG. 7 is a top perspective view of an embodiment of a clip-holder device according to the subject invention, showing a bent configuration which illustrates resulting central, right and left sections of the substrate layer, and four retaining clip portions integral with and affixed to the right and left sections of the substrate layer.

FIG. 7 is a front perspective view of an embodiment of a clip-holder device 30 in bent configuration as in FIG. 6, but being rotated clockwise approximately 90°. Shown are certain elements of the clip-holder device, including base 15 formed by substrate layer 35 and backing layer 39, two relief cuts 33 formed parallel to one another, providing a sectioned base comprising left section 36, central section 37 and right section 38, and tab 34 at an outer side edge of right section 38.

Figure 8:
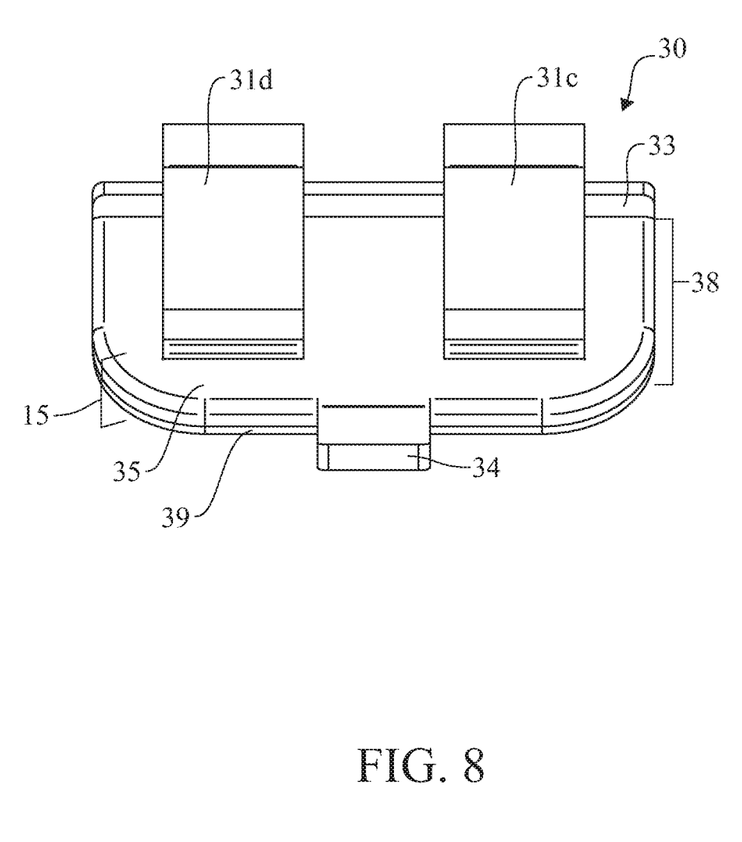
FIG. 8 is a side plan view of an embodiment of a clip-holder device according to the subject invention, in bent configuration, illustrating a right or left section of the substrate layer having two retaining clip portions integral with and affixed to the substrate layer.

FIG. 8 is a side plan view of an embodiment of a clip-holder device 30, in bent configuration, illustrating a right section 38 of the substrate layer having two retaining clip portions 31c and 31d integral with and affixed to the substrate layer 35. Also shown in this illustration are base 15 formed by substrate layer 35 and backing layer 39, relief cut 33, and tab 34 at an outer side edge of right section 38.

Figure 9:
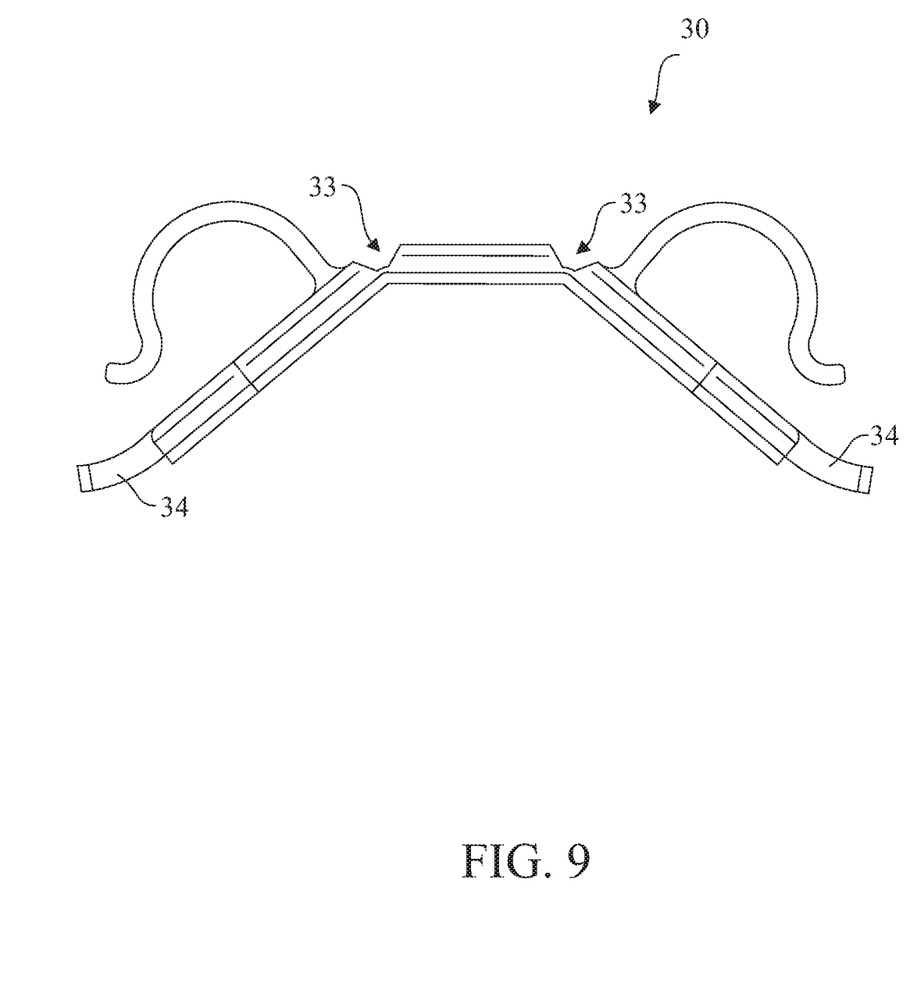
FIG. 9 is a side plan view of an embodiment of a clip-holder device according to the subject invention, in bent configuration, illustrating a right or left section of the substrate layer having two retaining clip portions integral with and affixed to the substrate layer.

FIG. 9 is an end plan view of an embodiment of a clip-holder device 30 according to the subject invention, in bent configuration, showing FIG. 8 rotated clockwise 90° illustrating right, central and left sections of the substrate layer divided by relief cuts 33 and tabs 34 comprising left section of the substrate layer having two retaining clip portions integral with and affixed to the substrate layer.

Figure 10:
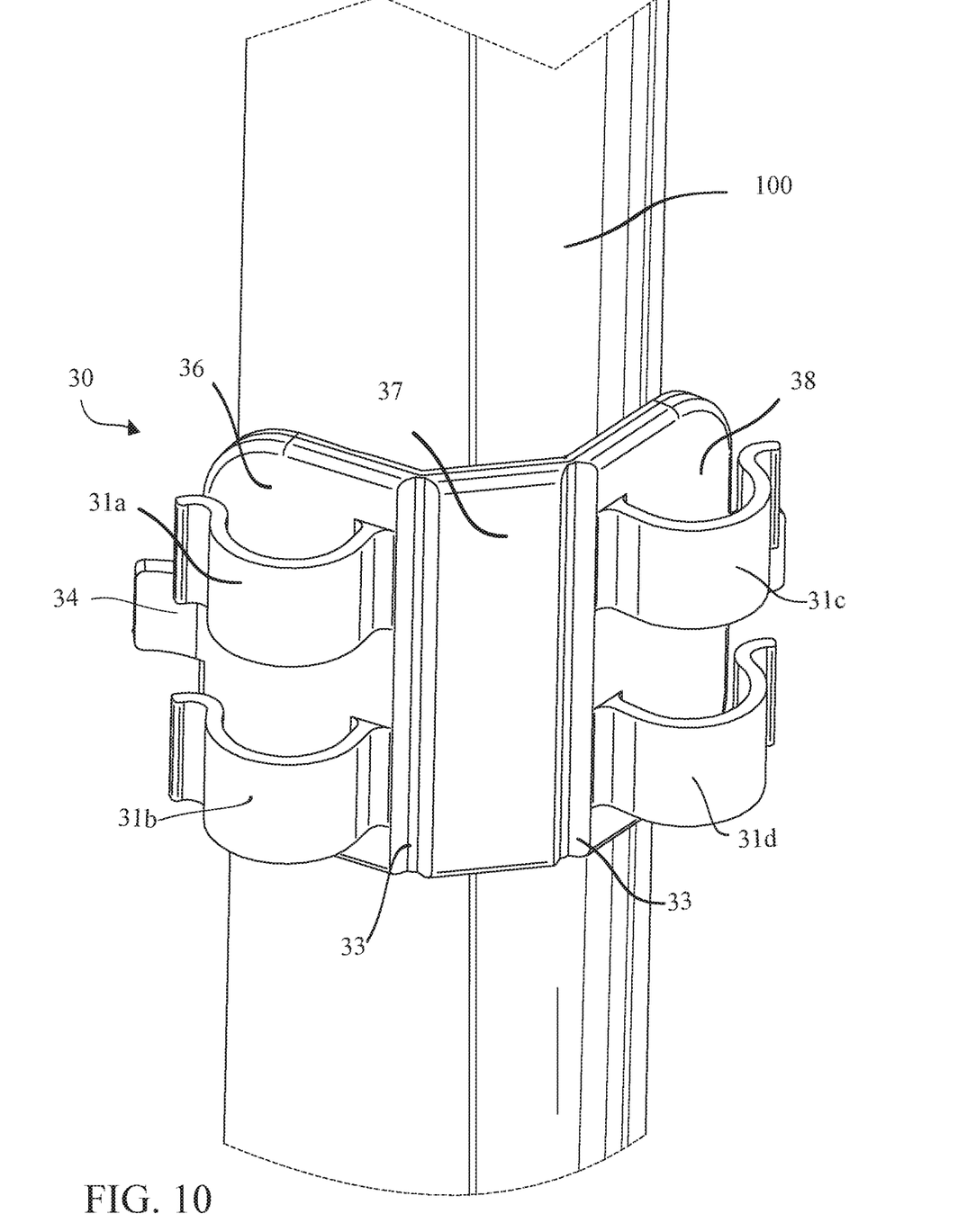
FIG. 10 is a perspective view of an of an embodiment of a clip-holder device according to the subject invention, in bent configuration, in use and as adhered to a cylindrical support structure, namely an IV pole.

FIG. 10 is a perspective view of an of an embodiment of a clip-holder device 30 according to the subject invention, in bent configuration, in use and as adhered to a cylindrical support structure 100, namely an IV pole. FIG. 10 illustrates how clip-holder 30, in bent configuration, engages and contacts a larger surface area of the support structure than if the base remained in a flat configuration. Specifically, the bent configuration facilitates the adhesive surface of the backing layer of each of left section 36, central section 37 and right section 38, formed by relief cuts 33, contacts and engages with the cylindrical support surface 100. Tab 34 can provide leverage for easy manipulation for removing of the clip-holder device, and replacement onto another support surface or the same support surface at a different location if needed. When positioned onto a support surface, retaining clip portions 31a-31d allow easy engagement of IV tubing so that the tubing can be moved away from an area where a medical or surgical procedure is being conducted, avoiding interference and entanglement by the IV tubing.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A device for retaining and positioning an IV set tubing in a location remote from a medical procedure area, said device comprising:
    a substantially flat and substantially rigid substrate layer having a front face and a back face, wherein said substantially flat and substantially rigid substrate layer comprises at least one tab to facilitate removal thereof and to guide placement of the tubing wherein the tab is formed integral with and extending substantially horizontally and curved or angled upwardly from a side edge of the substrate layer, the substrate layer further comprising one or more relief cuts enabling bending of the substantially flat and substantially rigid substrate layer to conform to a support structure having a rounded or curved surface, said substrate layer further comprising at least two retaining clip portions formed integral with the substrate layer and being configured as a hook, jutting away from said front face and forming a hold area configured for receiving and retaining an intravenous tubing without substantially impeding flow of fluid through said tubing, said retaining clip portions each having an opening for inserting a tubing into said hold area of the clip portion, each of the openings being opposed to one another and directed outwardly toward the edge of the substrate layer,
    a backing layer integral with or bonded to the back face of the substrate layer, said backing layer comprising an adhesive outer surface for detachably engaging a support structure;
    wherein the substrate layer and backing layer form a base which conforms, as desired, to a flat surface or a rounded or curved surface of the support structure.

2. The device of claim 1 wherein the substrate layer is substantially flat for adhering to a substantially flat support structure.

3. The device of claim 1 wherein the backing layer is pliable for conforming to a rounded or curved surface of the support structure.

4. The device of claim 1 comprising a plurality of retaining clip portions integral with the front face of the substrate layer.

5. The device of claim 4, comprising one to four retaining clip portions.

6. The device of claim 4, comprising four retaining clip portions configured as a first pair of retaining clip portions disposed parallel with one another on one side of the substrate layer, and a second pair of retaining clip portions disposed parallel with one another on an opposing side of the substrate layer.

7. The device of claim 1 wherein the relief cuts form a right section, central section, and left section of the substrate layer wherein the relief cuts allow for bending the base into a bended configuration for engaging the adhesive surface to a curved, rounded or cylindrical support structure.

8. The device of claim 1, wherein the device further comprises a removable protective cover disposed onto the adhesive surface for preventing inadvertent adherence of the adhesive.

9. The device of claim 8 wherein the removable protective cover is a peel-off sheet.

10. The device of claim 1, wherein the substrate layer of said device comprises two tabs extending substantially horizontally and curving upwardly from opposing side edges of the substrate layer to facilitate removal of the device which has been adhered to a support structure.

11. The device of claim 1 wherein the at least one tab facilitates placement of an IV tubing within a hold area of a retaining clip portion of the device.

12. The device of claim 10 wherein each tab serves as a guide for placement of an IV tubing within a hold area of a retaining clip portion of the device.

13. A method for retaining and positioning an IV set tubing in a location remote from a medical procedure area, said method comprising:
    providing a clip-holder device of claim 1; and
    adhering the clip-holder device onto a flat, curved, rounded, or cylindrical support structure
    whereby an IV tubing can be retained within a holding area formed in the retaining clip portion for preventing interference by or entanglement of the IV tubing.

14. A system for organizing and retaining an IV tubing while in use during a medical or surgical procedure, said system comprising:
    a clip-holder device of claim 1; and
    an IV set comprising IV tubing;
    wherein said clip-holder and IV set comprising IV tubing are packaged together.

15. The system of claim 14 wherein the packaging comprises written instructions for use of the clip-holder and IV tubing.

* * * * *